United States Patent
Hillmann

(10) Patent No.: US 9,241,813 B2
(45) Date of Patent: Jan. 26, 2016

(54) CONNECTING SYSTEM AND PROSTHESIS SYSTEM

(71) Applicant: OTTO BOCK HEALTHCARE GMBH, Duderstadt (DE)

(72) Inventor: Martin Hillmann, Duderstadt (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 14/352,836

(22) PCT Filed: Oct. 17, 2012

(86) PCT No.: PCT/EP2012/004340
§ 371 (c)(1),
(2) Date: Apr. 18, 2014

(87) PCT Pub. No.: WO2013/056824
PCT Pub. Date: Apr. 25, 2013

(65) Prior Publication Data
US 2015/0032226 A1 Jan. 29, 2015

(30) Foreign Application Priority Data

Oct. 19, 2011 (DE) .......................... 10 2011 116 280

(51) Int. Cl.
| | | |
|---|---|---|
| *A61F 2/78* | (2006.01) | |
| *A61F 2/80* | (2006.01) | |
| *A61F 2/50* | (2006.01) | |

(52) U.S. Cl.
CPC ................ *A61F 2/78* (2013.01); *A61F 2/7812* (2013.01); *A61F 2/80* (2013.01); *A61F 2002/5007* (2013.01); *A61F 2002/5018* (2013.01); *A61F 2002/5021* (2013.01); *A61F 2002/5073* (2013.01); *A61F 2002/5084* (2013.01);

(Continued)

(58) Field of Classification Search
CPC ........... A61F 2/78; A61F 2/7812; A61F 2/80; A61F 2002/7875
See application file for complete search history.

(56) References Cited

U.S. PATENT DOCUMENTS

| | | | |
|---|---|---|---|
| 6,051,026 A * | 4/2000 | Biedermann et al. ........... 623/38 |
| 6,589,288 B2 | 7/2003 | McDowell et al. |
| 6,979,354 B2 | 12/2005 | Wagman |

(Continued)

FOREIGN PATENT DOCUMENTS

| | | |
|---|---|---|
| CN | 1147370 A | 4/1997 |
| CN | 101224133 A | 7/2008 |

(Continued)

OTHER PUBLICATIONS

PCT International Search Report for PCT International Patent Application No. PCT/EP2012/004340, mailed Jan. 24, 2013.

(Continued)

*Primary Examiner* — Marcia Watkins
(74) *Attorney, Agent, or Firm* — Holland & Hart

(57) ABSTRACT

The invention relates to a connecting system for detachably connecting a prosthesis shaft to a liner that has been pulled over a residual limb, said system comprising a connecting pin and a receiving device with a receiving portion into which said connecting pin can be introduced, and being characterized in that the connecting pin comprises at least two rigid pin segments arranged one behind the other, in a longitudinal direction of said connecting pin, such that they can be displaced relative to one another.

18 Claims, 10 Drawing Sheets

(52) U.S. Cl.
CPC . *A61F2002/7875* (2013.01); *A61F 2220/0025* (2013.01)

(56) References Cited

U.S. PATENT DOCUMENTS

| | | |
|---|---|---|
| 2002/0116071 A1* | 8/2002 | Slemker et al. ............... 623/36 |
| 2004/0030410 A1 | 2/2004 | Wagman |
| 2004/0102856 A1 | 5/2004 | Hellberg |
| 2004/0138763 A1 | 7/2004 | Perkins et al. |
| 2004/0204771 A1* | 10/2004 | Swanson, Sr. ............... 623/901 |
| 2004/0243251 A1 | 12/2004 | Carstens |
| 2007/0168045 A1 | 7/2007 | Slemker et al. |
| 2007/0191965 A1 | 8/2007 | Colvin et al. |
| 2009/0306791 A1 | 12/2009 | Slemker et al. |
| 2011/0029096 A1 | 2/2011 | Laghi |

FOREIGN PATENT DOCUMENTS

| | | |
|---|---|---|
| CN | 101224134 A | 7/2008 |
| CN | 102137627 B | 9/2014 |
| EP | 1435880 B1 | 7/2004 |
| GB | 2338899 A | 1/2000 |
| WO | 03039398 A2 | 5/2003 |
| WO | 2006076011 A1 | 7/2006 |

OTHER PUBLICATIONS

Chinese Search Report for Chinese Patent Application No. 2012800501676.2, mailed Jun. 3, 2015 (2 pp.).

* cited by examiner

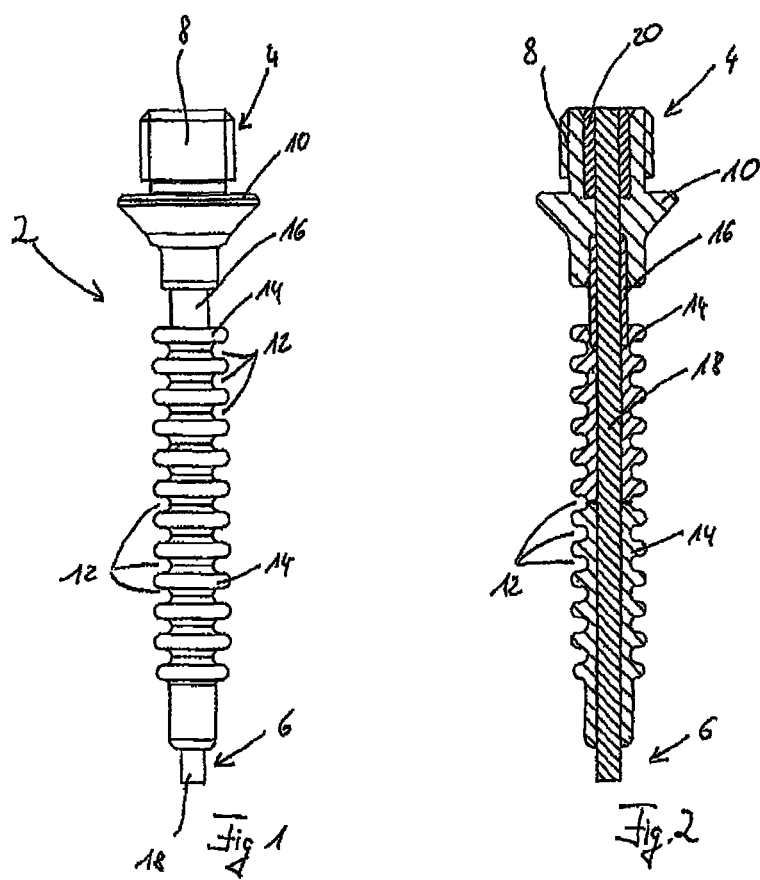

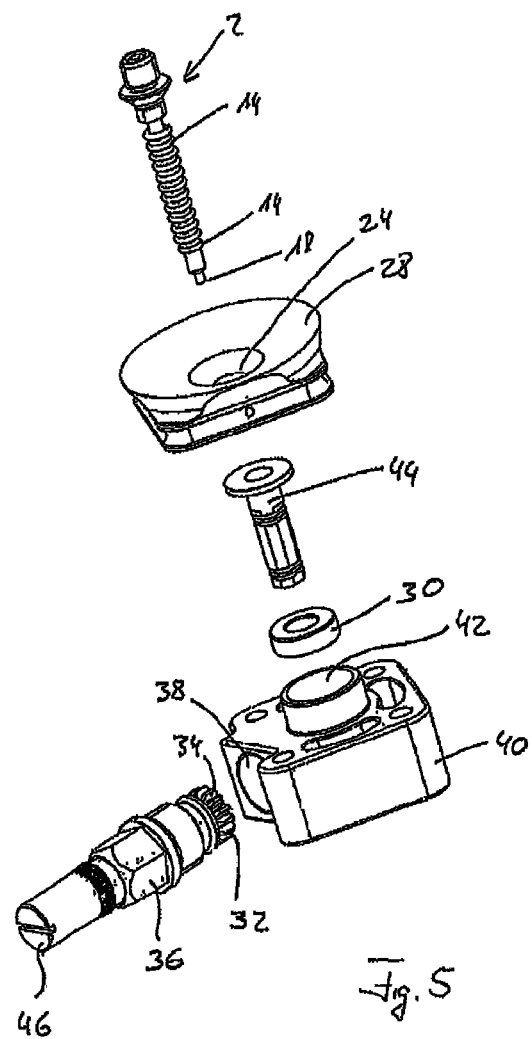

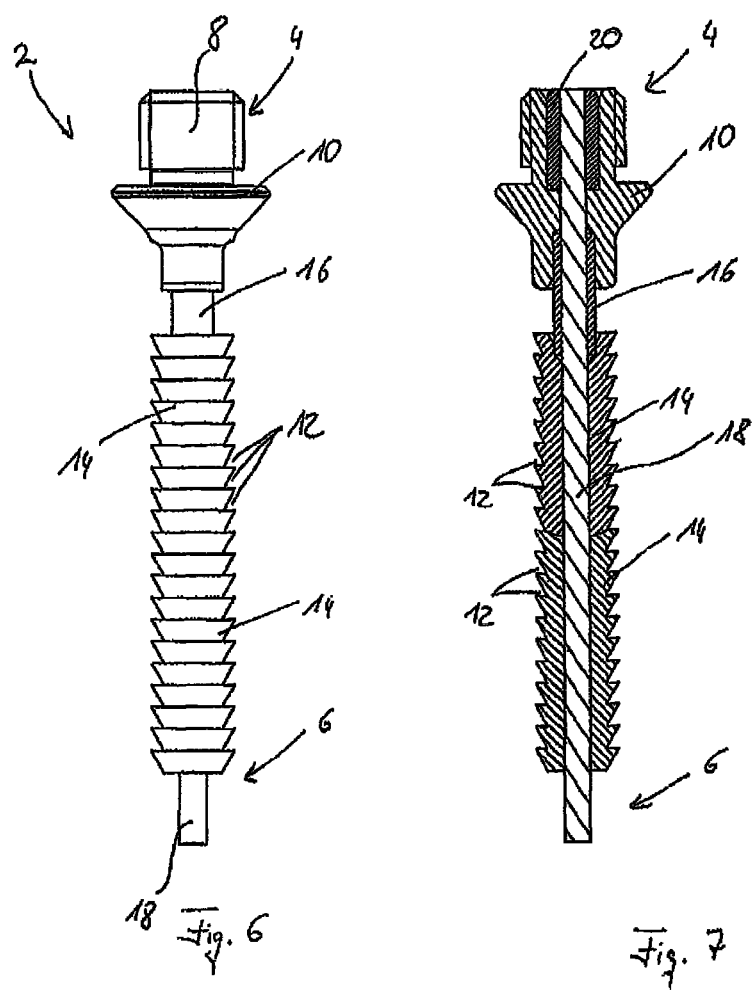

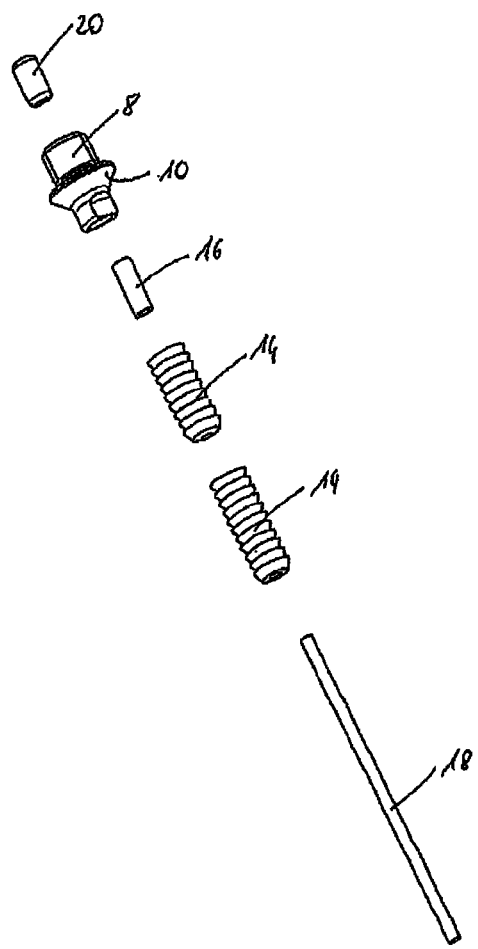
Fig: 8

CONNECTING SYSTEM AND PROSTHESIS SYSTEM

TECHNICAL FIELD

The invention relates to a connecting system for detachably connecting a prosthesis shaft to a liner that has been pulled over a residual limb, said system including a connecting pin and a receiving device with a receiving means into which the connecting pin can be inserted. The invention also relates to a prosthesis system having a liner and a prosthesis shaft, wherein the prosthesis system includes a connecting system of this type.

BACKGROUND

A generic connecting system is known, for example, from U.S. Pat. No. 6,979,354, B2 and WO 2006/076011 A1.

In order to fasten a prosthesis, for example a lower leg prosthesis, to a residual limb in a reliable manner, a liner, which can consist, for example, of a silicone material, is first of all pulled over said residual limb. A connecting pin, which can be connected to the liner in various ways, is situated at the distal end of the liner.

A receiving device, which includes a receiving means into which said connecting pin is insertable, is situated, on the other hand, on the prosthesis shaft. To connect the prosthesis shaft to the liner, the connecting pin is simply inserted into the receiving means that is provided for this purpose. In this case, the pin comprises circumferential grooves by way of which it is able to engage in a pinion or toothed wheel which is situated in the receiving device. As a result of the particular development of said receiving device, the pin is only able to be inserted into the receiving means in this way without, however, being able to simply be pulled out of it again. A pressure mechanism, for example, by means of which the pinion or the toothed wheel is moved out of engagement with the grooves of the connecting pin, has to be actuated for this purpose.

A disadvantage is that the liner cannot be pulled over the residual limb in an identical manner every time by the patient such that the connecting pin which is situated on the liner is also arranged in slightly different orientations on the residual limb. As a result, it is possible for the connecting pin to be oriented wrongly for it to be able to be inserted into the receiving means of the prosthesis shaft.

Consequently, it is known from U.S. Pat. No. 6,589,288 B2 to provide the connecting pin on its end that faces the residual limb with a ball which interacts like a ball-and-socket joint with the fastening arrangement, by means of which the connecting pin is secured to the liner. As a result, it is possible to pivot and displace the connecting pin laterally within tight boundaries.

A disadvantage is that, in particular as a result of the lateral displaceability of the pin, only very small deviations from the optimum position of the connecting pin on the residual limb are able to be compensated. As a result of the pivotability, however, it is possible for the connecting pin to be able to be moved into the receiving means of the receiving device even when it is clearly situated away from its optimum position. When inserting the connecting pin into the receiving means, the connecting pin is consequently pivoted to the side such that the distal tip, that is the end of the connecting pin that is remote from the residual limb, projects into the receiving means. As a result of the connecting pin, in this case, however, having a clear angular deviation from its optimum position, it is possible that it cannot be inserted completely into the receiving means, which results in non-optimum fastening of the prosthesis shaft on the residual limb. Sore points and pain as well as wrong loads and wrong positions on the patient occur as a result.

In order to counter said problem, it is known from EP 1 435 880 B1 to develop the connecting pin in a totally flexible manner. It is formed, for example, from a synthetic material or as a helical spring and is realized so as to be flexible in every plane that coincides with its longitudinal axis and also so as to be elastically flexible in the axial direction. Consequently, a connecting pin of this type is able to compensate up to a certain degree for any wrong position and wrong positioning of the connecting pin relative to the receiving means of the receiving device. However, a disadvantage is that as a result of the flexibility and elasticity of the connecting pin which is necessary for this and is effective in all directions, the pressure stability thereof is clearly reduced. In particular when inserting the connecting pin into the receiving means of the receiving device when putting on the prosthesis system, the connecting pin can consequently buckle outward, instead of being inserted further into the receiving means. This results in the prosthesis shaft only being fastened to the liner in a very poor manner and additionally in wrong pressure loads and, where applicable, pressing points on the residual limb of the patient.

SUMMARY

Consequently, the object underlying the invention is to propose a connecting system with which slightly wrong positions and wrong positioning of the liner and consequently of the connecting pin relative to the prosthesis shaft are able to be compensated, and nevertheless the necessary reliability is ensured such that the prosthesis shaft is able to be put on in a reliable and fault-free manner.

The invention achieves the object set by a generic connecting system which is distinguished in that the connecting pin includes at least two rigid pin segments which are arranged one behind another so as to be displaceable toward one another along a longitudinal direction of the connecting pin, that is from the first end thereof to the second end thereof.

By using at least two rigid pin segments which are themselves therefore not realized in a flexible or elastic manner, it is possible to ensure the necessary pressure stability which is required in particular when inserting the connecting pin into the receiving means of the receiving device. As the individual pin segments, however, are displaceable toward one another, that is in particular are tiltable or pivotable toward one another, sufficient flexibility is provided to be able to compensate for wrong positions and wrong positioning of the connecting pin relative to the receiving device. In order to mount the pin segments in such a manner, it can also be necessary to mount them so as to be displaceable toward one another.

The use of precisely two rigid pin segments in particular has proved to be advantageous. When using only one rigid pin segment, pivoting toward one another is not possible. A solution of this type is known from the prior art and leads to the named problem. If more than two rigid pin segments are used, the number of points at which two adjacent pin segments can be pivoted toward one another is naturally also increased. In particular if the connecting pin is not inserted precisely into the receiving means of the receiving device, at least part of the connecting pin can break off outward in said development. Thus, it is possible, for example, for the pin segment which is inserted first into the receiving means, to be held in the receiving means while the second and third pin segments are pivoted out outward and thus prevent the connecting pin from being inserted deeper into the receiving means. This only leads to a connection between the prosthesis shaft and the liner which is very unreliable. Nevertheless, a precise connection that is usable flexibly in many orientations is also possible in said development.

In a preferred embodiment the individual pin segments are threaded onto a flexible guide element. This can be, for example, a cable element, for example a steel cable or a plastics material cable. The individual pin segments can be threaded like pearls on a chain onto said guide element such that they are displaceable, in particular tiltable and pivotable, toward one another.

The connecting pin preferably comprises a first end for arranging on the liner and a second end which is opposite the first end, and the pin segments are pretensioned by a tensioning element in the direction of the second end. In this case, the tensioning element can include, for example, a spring, in particular a helical spring, or an elastomer, for example in the form of a hose. In a preferred manner, the tensioning element is realized in the form of an elastic hose. The tensioning element is also threaded onto the flexible guide element in a particularly simple embodiment.

As a result of the tensioning element, it is possible to pivot or tilt the at least two pin segments, which are threaded onto the guide element, toward one another.

In an advantageous manner, a connecting element for connecting the connecting pin to the liner is situated on the first end of the connecting pin which faces the liner. This can be, for example, an external thread such that the connecting element is screwed into a corresponding thread on the liner that is provided for this purpose. All other possibilities to secure the connecting pin on the liner are naturally also conceivable.

In a particularly preferred manner, the tensioning element is arranged between the pin segments and the first end of the connecting pin. Consequently the tensioning element is situated closer to the liner than the individual pin segments.

The pin segments preferably comprise a plurality of grooves which run around the longitudinal direction and are realized in order to engage in a pinion which is provided in the receiving device or a toothed wheel or a similar device, wherein the pinion or the toothed wheel or the device is movable into a insertion position in which the connecting pin is insertable into the receiving device, and into a release position in which the connecting pin is removable out of the receiving device.

These types of arrangements where a pinion is movable into an insertion position and a release position are known from the prior art. Together with the particular arrangement of the pin segments and with the tensioning element along the guide element, several advantages are formed, however, in relation to the solutions known from the prior art.

When the prosthesis is put on, the connecting pin, which is arranged on the liner, is inserted into the receiving means of the receiving device. The individual grooves of the pin segments engage in the pinion when the connecting pin is inserted into the receiving means. Lateral buckling is prevented in an effective manner by the rigid segments used.

When walking with the prosthesis, the pin is pressure loaded when the prosthesis is trodden on. In this case, it is consequently pressed further in the direction of the receiving means of the receiving device and, where applicable, penetrates deeper into said receiving means. In said phase of the walking, an optimum seat and hold of the connecting pin in the receiving means is consequently achieved. In the swing phase of every step, the connecting pin is put under tensile load. As the connecting pin, however, is not realized in an elastic manner along its longitudinal axis, a relative movement between the prosthesis shaft and the liner does not occur here. As a result, chafing or rubbing of the prosthesis shaft against the liner and consequently against the residual limb of the patient is avoided, as a result of which wearing comfort is clearly increased.

In an advantageous manner the receiving device comprises an insertion device by means of which the orienting and/or the positioning of the connecting pin in the receiving means is simplified. This can be, for example, an element that is developed in a funnel-shaped manner, by means of which the second end of the connecting pin is guided into the receiving means of the receiving device as soon as it is situated inside the funnel.

As an alternative to this or in addition to it, the insertion device can include at least one magnetic element and the connecting pin can consist at least in part of a material onto which a force is exerted as a result of the magnetic element, by means of which force the connecting pin is aligned onto the receiving means. Thus, it is conceivable, for example, to arrange a permanent magnet on the receiving device in the vicinity of the receiving means and also to arrange a permanent magnet on the connecting pin, preferably in the vicinity of its second end. Both should be aligned in this case such that opposite poles are aligned with respect to one another. An attraction force is produced as a result by means of which the connecting pin is introduced in a particularly simple manner into the receiving means of the receiving device. Naturally, where a suitable material selection is made it is sufficient to provide only one permanent magnet. As an alternative to this or in addition to it, it is also possible to provide on the receiving device a ring-shaped magnetic element which is placed around the receiving means. If then, for example, the second end of the connecting pin is of a material onto which a force is exerted as a result of said magnetic element, the connecting pin, and in particular the second end thereof, is centered toward the actual receiving means. The inserting of the connecting pin into the receiving means is further simplified as a result.

A prosthesis system according to the invention having a liner and a prosthesis shaft additionally includes a connecting system described here, wherein the connecting pin is arranged on the liner and the receiving device is arranged on the prosthesis shaft.

BRIEF DESCRIPTION OF THE DRAWINGS

An exemplary embodiment of the present invention is described below by means of a drawing, in which, in detail:

FIG. 1—shows the schematic view of a connecting pin for a connecting system according to a first exemplary embodiment of the present invention, FIG. 2—shows a schematic sectional representation through the connecting pin from FIG. 1, FIG. 3—shows an exploded drawing of the connecting pin from FIGS. 1 and 2, FIG. 4—shows a schematic sectional representation through a connecting system according to a further exemplary embodiment of the present invention, FIG. 5—shows an exploded drawing of a connecting system according to an exemplary embodiment of the present invention, FIG. 6—shows the schematic view of a connecting pin for a connecting system according to a further exemplary embodiment of the present invention, FIG. 7—shows a schematic sectional representation through the connecting pin from FIG. 6, FIG. 8—shows an exploded drawing of the connecting pin from FIGS. 6 and 7, FIG. 9—shows an exploded drawing of a connecting pin for a connecting system according to a further exemplary embodiment of the present invention, FIG. 10—shows a schematic sectional representation through a connecting system according to a further exemplary embodiment of the present invention, FIG. 11—shows an exploded drawing of a prosthesis system according to an exemplary embodiment of the present invention and FIG. 12—shows a schematic sectional representation through the prosthesis system from FIG. 11.

DETAILED DESCRIPTION

Figure 3:
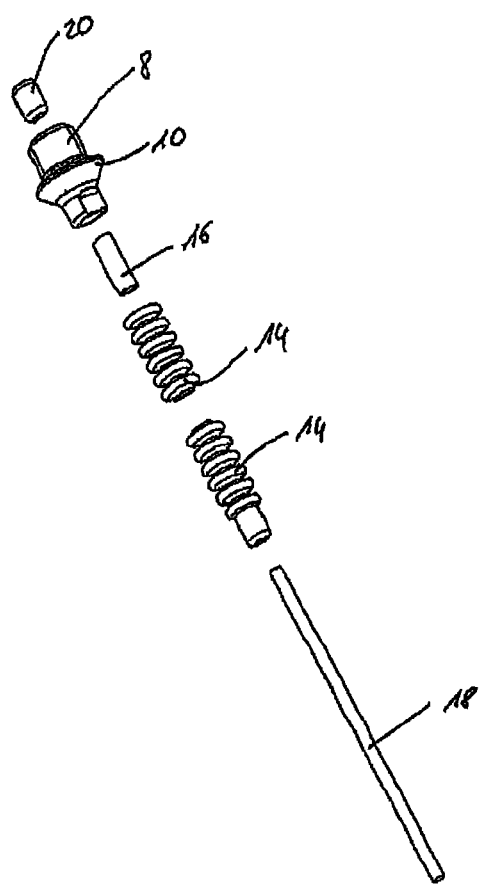

FIG. 1 shows the schematic view of a connecting pin 2 for a connecting system according to a first exemplary embodiment of the present invention.

The connecting pin 2 has a first end 4 for arranging on a liner as well as a second end 6 by way of which the connecting pin is insertable into a receiving means of a receiving device. A connecting element 8 by way of which the connecting pin 2 can be secured on the liner is shown on the first end 4. This can occur, for example, in the form of a screw connection. In this case, for example, the connecting element 8 has an external thread.

In FIG. 1, below the connecting element 8, there is a stop 10, by way of which the connecting pin 2 abuts against the liner when it is connected to the liner by means of the connecting element 8.

The connecting pin 2 has over its length a plurality of grooves 12 which run round in its longitudinal direction. Said grooves are arranged on two pin segments 14 which are arranged one behind the other along a longitudinal direction of the connecting pin 2. Between the first end 4 and the two pin segments 14 there is a tensioning element 16 which, in the exemplary embodiment shown, is realized as an elastic hose. As an alternative to this, the tensioning element 16 can also be realized, for example, in the form of a helical spring.

Both the tensioning element 16 and the pin elements 14 are threaded onto a flexible guide element 18, only a small portion of which can be seen in FIG. 1 on the second end 6.

FIG. 2 shows a sectional representation of the representation from FIG. 1. It can be seen that the flexible guide element 18 runs through from the first end 4 up to the second end 6 of the connecting pin 2. All the other components are threaded onto said flexible guide element 18 and fastened to it. It can clearly be seen better in FIG. 2 that the grooves 12 are arranged on two pin segments 14 as shown one above another in FIG. 2.

If the connecting pin 2 is then inserted into a receiving means, with respect to which it is not positioned in an optimum manner, said wrong positioning is able to be compensated as a result of the two pin segments 14 being arranged so as to be displaceable toward one another. To this end, for example, the flexible guide element 18 is bent such that the pin segments 14 arranged thereon are pushed slightly apart from one another. At the same time in this case, the tensioning element 16 is curved or, if it is realized as a helical spring, lightly compressed. The flexibility of the connecting pin 2 is ensured as a result without giving up too much of the necessary pressure stability. As a result of the particular development, the pin segments 14 are pivotable and tiltable toward one another in all directions without the overall length of the connecting pin 2, that is from its first end 4 to its second end 6, being modified. As a result, a relative movement between the liner and the prosthesis shaft is restricted at least severely, in the optimum case even totally.

The flexible guide element 18 is fastened at the first end 4 by means of a securing means 20. This can be, for example, a screw-type or adhesive-type connection or a solder or welding connection. The overall length, that is the distance from the first end 4 to the second end 6 of the connecting pin 2, is fixed as a result. In said form it is not realized so as to be elastic along its longitudinal axis. As a result, when walking using a prosthesis which is secured to the liner as a result of a connecting pin of this type, there is no relative movement between the prosthesis shaft and the liner such that wounds cannot also be caused on the residual limb of the patient by chafing or wrong pressure load.

FIG. 3 shows an exploded drawing of the connecting pin 2 from FIGS. 1 and 2. The two pin segments 14 are pushed onto the flexible guide element 18. The tensioning element 16 and the connecting element 8 and the stop 10 are situated in the region of the first end 4, that is in the top end in FIG. 3, of the connecting pin 2, the flexible guide element 18 being secured on the connecting element 8 by means of the securing means 20.

Figure 4:
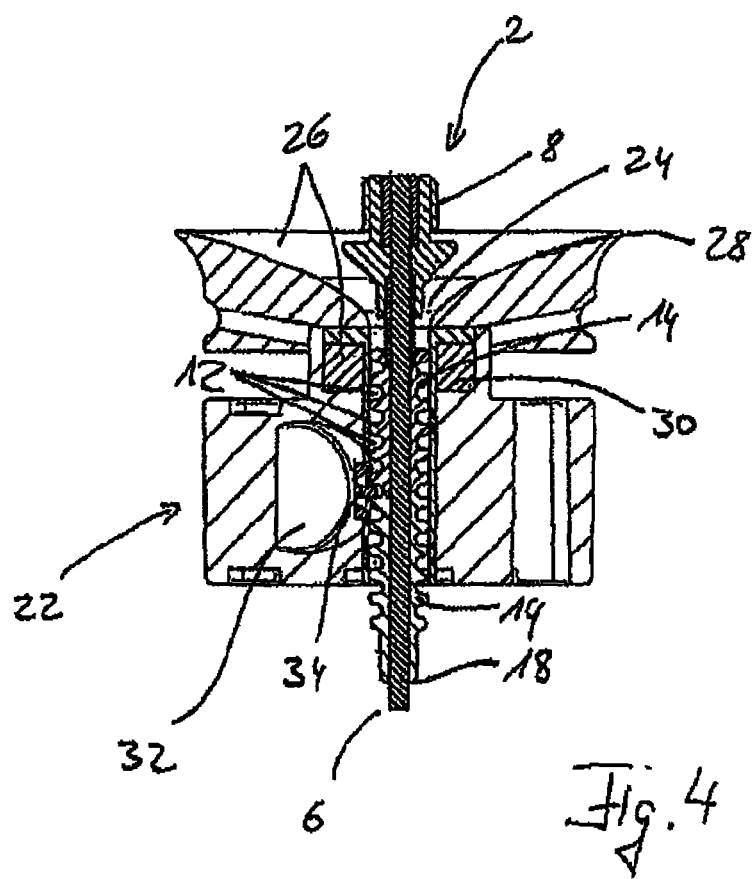

FIG. 4 shows a sectional representation through a connecting system according to an exemplary embodiment of the present invention. The connecting pin 2 with its connecting element 8 is situated centrally on the second end 6. The two pin segments 14 are situated along its flexible guide element 18. Embodiments with more than two, for example three, four or five pin segments 14 are naturally also conceivable. Depending on the desired length of the connecting pin 2, other numbers of pin segments 14 can also be used.

A receiving device 22 is shown around the connecting pin 2. Said receiving device comprises in the upper portion a receiving means 24 into which the connecting pin 2 is inserted. The receiving means 24, in this case, has an insertion device 26 which consists of two elements in FIG. 4. On the one hand, the receiving device 22 is realized around the receiving means 24 in the form of a funnel 28. On the other hand, a magnetic element 30, which includes in a ring-shaped manner the receiving means 24 and consequently, in the state shown in FIG. 4, also the connecting pin, is arranged around the actual receiving means 24. As an alternative to this or in addition to it, a further magnetic element 30, which is not shown, however, in FIG. 4, can be provided. In this case, this can be, for example, a cylindrical magnetic element by means of which a force, which pulls the second end 6 of the connecting pin 2 into the receiving means 24, is exerted onto the connecting pin 2.

One component of the connecting pin 2 is produced from a material onto which a force is exerted as a result of the magnetic element 30. In the embodiment shown, the second end 6 is centered in the direction of the receiving means 24 in this way when the connecting pin 2 is inserted.

A pinion 32 is shown schematically in the bottom part of the receiving device 22. The pinion 32 has teeth 34 which engage in the grooves 12 of the pin segments 14. In the state shown in FIG. 4, the pinion 32 is situated in the insertion position.

In said position it is possible to insert the connecting pin in the exemplary embodiment shown in FIG. 4 from above into the receiving device 22. The teeth 34 of the pinion 32 engage in the groove 12 and the pinion 32 is realized so as to be able to rotate in the direction necessary for this. A rotation of the pinion 32 in the opposite direction, however, is not possible. As a result the connecting pin 2, for example during the swing phase of a step, is prevented simply from being pulled out of the receiving device 22 again.

FIG. 5 shows an exploded drawing of the connecting system shown in FIG. 4. The pinion 32 with the teeth 34 situated therein is arranged on a latching unit 36 which is inserted into an opening 38 of a locking plate 40 that is provided for this purpose. Perpendicular to the opening 38, the locking plate 40 comprises a central bore 42 into which both the magnetic element 30 and a press-fit bush 44 are inserted. The press-fit bush 44 ends in the top region with the receiving means 24 into which the connecting pin 2 is inserted.

If the pinion 32 is situated in the insertion position, its teeth 34 engage in the grooves 12 of the pin segments 14. A control element 46, by means of which the latching unit 36 is able to be rotated about its longitudinal axis, is shown on the end of the latching unit 36 remote from the pinion 32. To this end, a screwdriver, a coin or a similar suitable tool has to be inserted into the slot provided in the control unit 46. The entire latching unit 36 can be rotated as a result of rotating said tool. This is possible, however, only in one direction. By rotating in said one direction, the connecting pin 2 is pulled still further into the receiving means 24 of the receiving device 22. Rotation in the other direction is prevented in order to exclude the connecting pin 2 being conveyed out of the receiving means 24 of the receiving device 22.

If the pinion 32 is to be moved from the insertion position into the release position, it is conceivable, for example, by pressing the control element 46 in the direction of the locking plate 40, to move the pinion out of engagement with the grooves 12 of the pin segments 14. In said case, the connecting pin 2 can simply be pulled upward out of the receiving means 24.

FIG. 6 shows a further embodiment of the connecting pin 2. It differs from the representation in FIG. 1 in particular by the form of the grooves 12. These are not realized, as in FIG. 1, in a U-shaped manner, but comprise a sawtooth-like form. In this case, it can be seen in FIG. 6 that each groove 12 comprises an inclinedly extending flank and a horizontally extending flank.

FIG. 7 shows a schematic sectional representation through the connecting pin 2 from FIG. 6. Said representation also differs from the representation in FIG. 2 substantially by the form of the individual grooves 12. If the connecting pin 2 according to FIGS. 6 and 7 is inserted into a receiving device 22 or the receiving means 24 thereof, it does not engage in a pinion which is rotated as a result of pushing in the connecting pin 2, but moves into engagement with a toothed projection or similar which snaps into the individual grooves 12 and thus counters the connecting pin 2 being pulled out of the receiving means 24, that is an upward movement in FIGS. 6 and 7.

FIG. 8 shows an exploded drawing of the connecting pin 2 from FIGS. 6 and 7. It can be seen that the connecting pin 2 does not differ in design from the connecting pin 2 from FIGS. 1 to 3, but the pin segments 14 simply have a different type of grooves 12.

Figure 9:
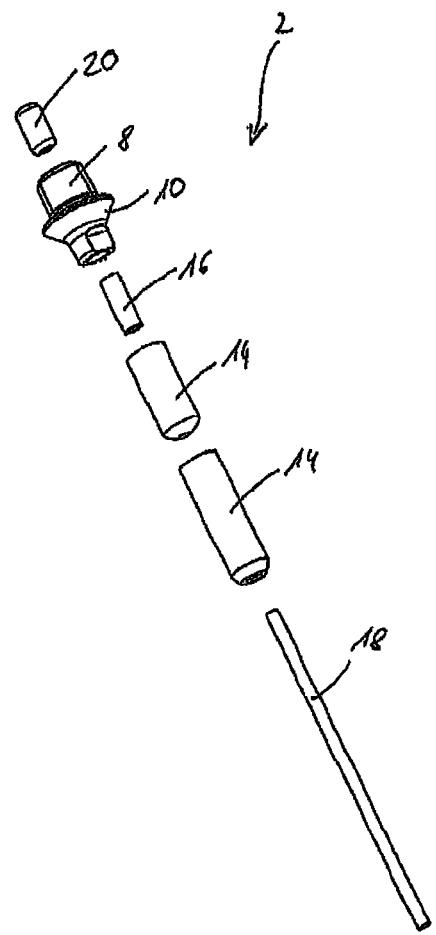

FIG. 9 shows an exploded drawing of a further embodiment of the connecting pin 2. Said connecting pin 2 does not differ in design from the previously shown connecting pins 2 either. The difference is purely that the individual pin segments 14 in the exemplary embodiment shown in FIG. 9 do not comprise any grooves 12, but have a smooth outside surface. If a connecting pin 2 of this type is inserted into the receiving means 24 of the receiving device 22 provided for this purpose, the pin segments 14 cannot be moved to engage with a toothed element or a pinion. In this case, the connecting pin 2 is prevented from being pulled out of the receiving means 24 as a result of a clamping mechanism.

Figure 10:
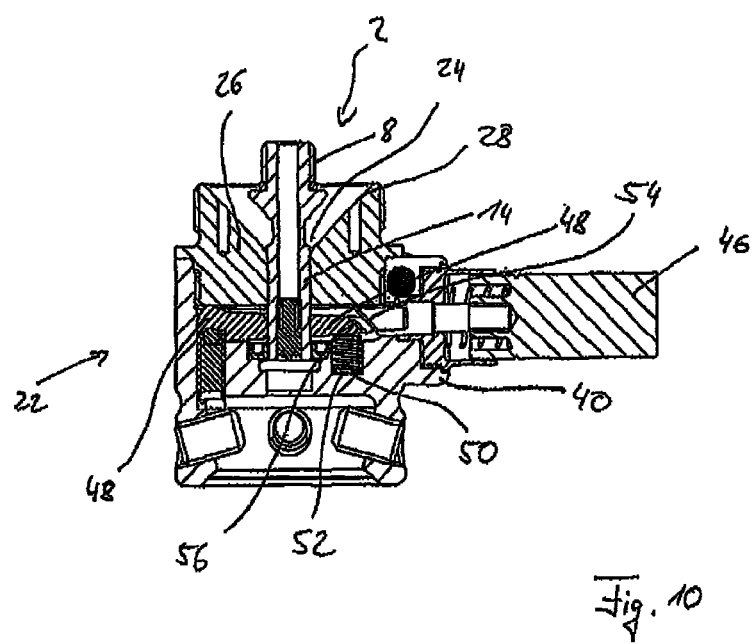

Said clamping mechanism is shown in FIG. 10 in a schematic sectional representation through the connecting system. The connecting pin 2 which is arranged in the receiving device 22 can be seen. The receiving device 22 comprises the insertion device 26 and the funnel 28 again in order to be able to insert the connecting pin 2 in as comfortable and simple a manner as possible into the receiving device 22 or the receiving means 24 thereof.

Differently to in the representation of FIG. 4, the pin segments 14 in the exemplary embodiment shown in FIG. 10 comprise a smooth outside surface. When inserted into the receiving means 24, the connecting pin 2 is guided through a clamping washer 48 which is arranged in the receiving device 22. Said clamping washer has a central bore through which the connecting pin 2 is guided.

FIG. 10 shows that the clamping washer 48 is mounted in its right-hand region on a clamping spring 50. The clamping spring 50 is a compression spring which is arranged in a recess 52 provided for that purpose. The clamping spring 50 presses the right-hand region of the clamping washer 48 upward such that the connecting pin 2 is tilted in the central bore of the clamping washer 48. As a result, the connecting pin 2 is prevented in a reliable manner from being pulled out, upward in FIG. 10.

If, on the other hand, the connecting pin 2 is to be inserted further into the receiving means 24, a force is also applied onto the clamping washer 48 as a result such that the clamping spring 50 is compressed and in this manner the tilting eliminated.

In order to remove the connecting pin 2 out of the receiving means 24 again, the control element 46 is arranged on the locking plate 40. On its end that faces the interior of the receiving device 22, said control element comprises a first bevel 54. The first bevel 54 is in contact with a second bevel 56 which is provided on the clamping washer 48. If the control element 46 is then moved in the direction of the connecting pin 2, which has been moved into the receiving means 24, the first bevel 54 and the second bevel 56 slide toward one another, as a result of which the right-hand region of the clamping washer 48 is moved downward and this compresses the clamping spring 50. As a result, the tilting of the connecting pin 2 in the clamping washer 48 is lifted such that the connecting pin 2 is able to be removed out of the receiving means 24.

Figure 11:
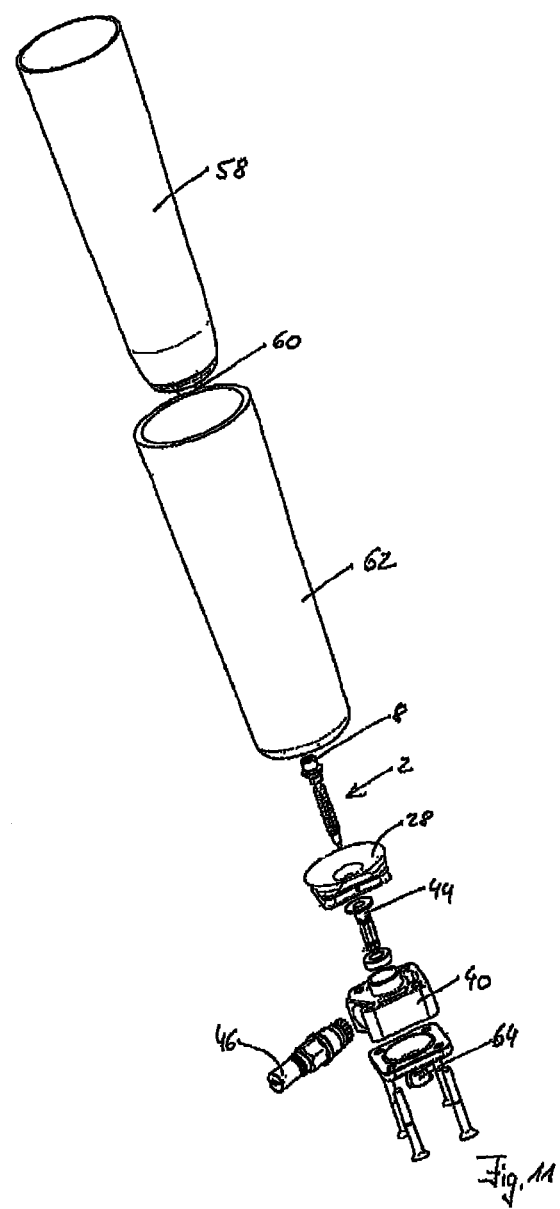

FIG. 11 shows an exploded drawing of a prosthesis system according to an exemplary embodiment of the invention. It is possible to see a liner 58, at the bottom end of which a fastening device 60 is situated, on which the connecting element 8 of the connecting pin 2 is able to be arranged. The liner 48 is arranged in a prosthesis shaft 62, at the bottom end of which the receiving device 22 is arranged, as is shown, for example, in FIG. 5. The actual artificial limb is arranged by means of further connecting means 64 at the bottom end of the locking plate 40.

Figure 12:
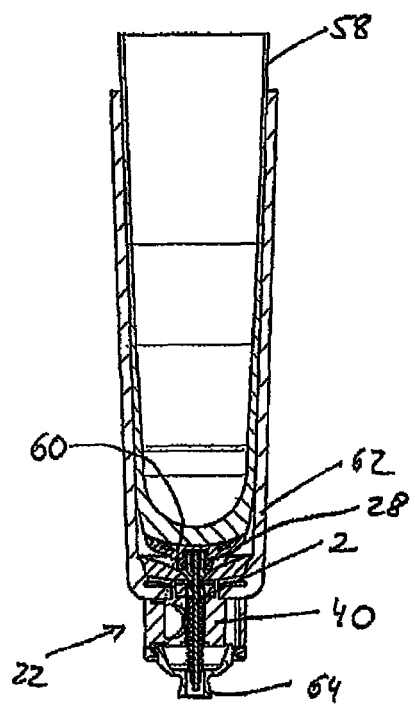

FIG. 12 shows a sectional representation through the prosthesis system which is shown in the form of an exploded drawing in FIG. 11. The liner 58 on which the fastening device 60 for the connecting pin 2 is situated can be seen. The liner 58 is arranged in the prosthesis shaft 62, at the bottom end of which is situated the receiving device 22. In the state shown in FIG. 12, the connecting pin 2 is inserted into the receiving device 22 or into the receiving means 24 thereof.

---

List of references

2 Connecting pin
4 First end
6 Second end

List of references

8 Connecting element
10 Stop
12 Groove
14 Pin segment
16 Tensioning element
18 Flexible guide element
20 Securing means
22 Receiving device
24 Receiving means
26 Insertion device
28 Funnel
30 Magnetic element
32 Pinion
34 Teeth
36 Latching unit
38 Opening
40 Locking plate
42 Central bore
44 Press-fit bush
46 Control element
48 Clamping washer
50 Clamping spring
52 Recess
54 First bevel
56 Second bevel
58 Liner
60 Fastening device
62 Prosthesis shaft
64 Connecting means
FR/ad

The invention claimed is:

1. A connecting system for detachably connecting a prosthesis shaft to a liner that has been pulled over a residual limb, the system comprising:
a connecting pin;
a receiving device with a receiving member into which the connecting pin can be inserted;
wherein the connecting pin includes at least two rigid pin segments which are arranged one behind another so as to be displaceable by tilting or pivoting relative to each other with respect to a longitudinal direction of the connecting pin, and the pin segments are threaded onto a flexible guide element.

2. The connecting system as claimed in claim 1, wherein the connecting pin comprises a first end for arranging on the liner and a second end which is opposite the first end, and the pin segments are prestressed by a tensioning element in the direction of the second end.

3. The connecting system as claimed in claim 2, wherein the tensioning element includes a spring or an elastomer.

4. The connecting system as claimed in claim 3, wherein the spring is a helical spring, and the elastomer has a hose shape.

5. The connecting system as claimed in claim 2, wherein the tensioning element is threaded onto the flexible guide element.

6. The connecting system as claimed in claim 5, wherein the tensioning element is arranged between the pin segments and the first end of the connecting pin.

7. The connecting system as claimed in claim 1, wherein the pin segments comprise a plurality of grooves which run around the longitudinal direction and are configured to engage in a pinion which is provided in the receiving device, wherein the pinion is movable into an insertion position in which the connecting pin is insertable into the receiving device, and into a release position in which the connecting pin is removable out of the receiving device.

8. The connecting system as claimed in claim 1, wherein the receiving device comprises an insertion device configured to simplify at least one of orienting and positioning the connecting pin in the receiving member.

9. The connecting system as claimed in claim 8, wherein the insertion device includes at least one magnetic element, and the connecting pin consists at least in part of a material onto which a force is exerted as a result of the at least one magnetic element.

10. A prosthesis system having a liner and a prosthesis shaft, wherein the prosthesis system includes a connecting system as claimed in claim 1, and the connecting pin is arranged on the liner and the receiving device is arranged on the prosthesis shaft.

11. A connecting system configured to detachably connect a prosthesis shaft to a liner, the liner being configured to be positioned on a residual limb, the system comprising:
a connecting pin comprising:
a first end configured to be coupled to the liner;
a second end;
at least two rigid pin segments that are arranged in series, the pin segments being displaceable by tilting or pivoting relative to each other with respect to a longitudinal direction of the connecting pin, the pin segments being threaded onto a flexible guide element;
a receiving device having a receiving cavity into which the second end of the connecting pin is inserted, the receiving device being cg to be coupled to the prosthesis shaft.

12. The connecting system as claimed in claim 11, wherein the pin segments are prestressed by a tensioning element in a direction of the second end.

13. The connecting system as claimed in claim 12, wherein the tensioning element includes a spring or an elastomer.

14. The connecting system as claimed in claim 12, wherein the tensioning element is threaded onto the flexible guide element.

15. The connecting system as claimed in claim 14, wherein the tensioning element is arranged between the pin segments and the first end of the connecting pin.

16. The connecting system as claimed in claim 11, wherein the pin segments comprise a plurality of grooves which run around the longitudinal direction and are configured to engage in a pinion which is provided in the receiving device, wherein the pinion is movable into an insertion position in which the connecting pin is insertable into the receiving device, and into a release position in which the connecting pin is removable out of the receiving device.

17. The connecting system as claimed in claim 11, wherein the receiving device comprises an insertion device configured to simplify at least one of orienting and positioning the connecting pin in the receiving member.

18. The connecting system as claimed in claim 17, wherein the insertion device includes at least one magnetic element, and the connecting pin comprises a material onto which a force is exerted as a result of the at least one magnetic element.

* * * * *